United States Patent [19]

Lukasavage et al.

[11] Patent Number: 5,250,687
[45] Date of Patent: Oct. 5, 1993

[54] PROCESS FOR PREPARATION OF RDX

[75] Inventors: William J. Lukasavage, Las Vegas, Nev.; Steven Nicolich, Saddle Brook; Norman Slagg, Wayne, both of N.J.

[73] Assignee: The United States of America as represented by the Secretary of the Army, Washington, D.C.

[21] Appl. No.: 936,375

[22] Filed: Aug. 28, 1992

[51] Int. Cl.$^5$ ............................................. C07D 251/06
[52] U.S. Cl. ................................... 544/215; 544/180; 544/185
[58] Field of Search .......................................... 544/215

[56] References Cited

U.S. PATENT DOCUMENTS 3,937,703  2/1976  Meredith .............................. 544/215

OTHER PUBLICATIONS

Suri et al., Synthesis, 9, 743–5, 1988.
Cooney et al., J. Chem. Soc. Perkin Trans. II, 77–81 1989.

Primary Examiner—Mukund J. Shah
Assistant Examiner—Y. N. Gupta
Attorney, Agent, or Firm—Anthony T. Lane; Edward Goldberg; Michael C. Sachs

[57] ABSTRACT 1,3,5-TRINITROHEXAHYDRO-1,3,5-TRIAZINE (RDX) is prepared in a new simplified and efficient manner which provides near quantitative yield. Our process is based upon the nitration of 3,7-DIACETYL 1,3,5,7 TETRAAZA[3.3.1.]BICYCLONONANE (DAPT).

5 Claims, 1 Drawing Sheet

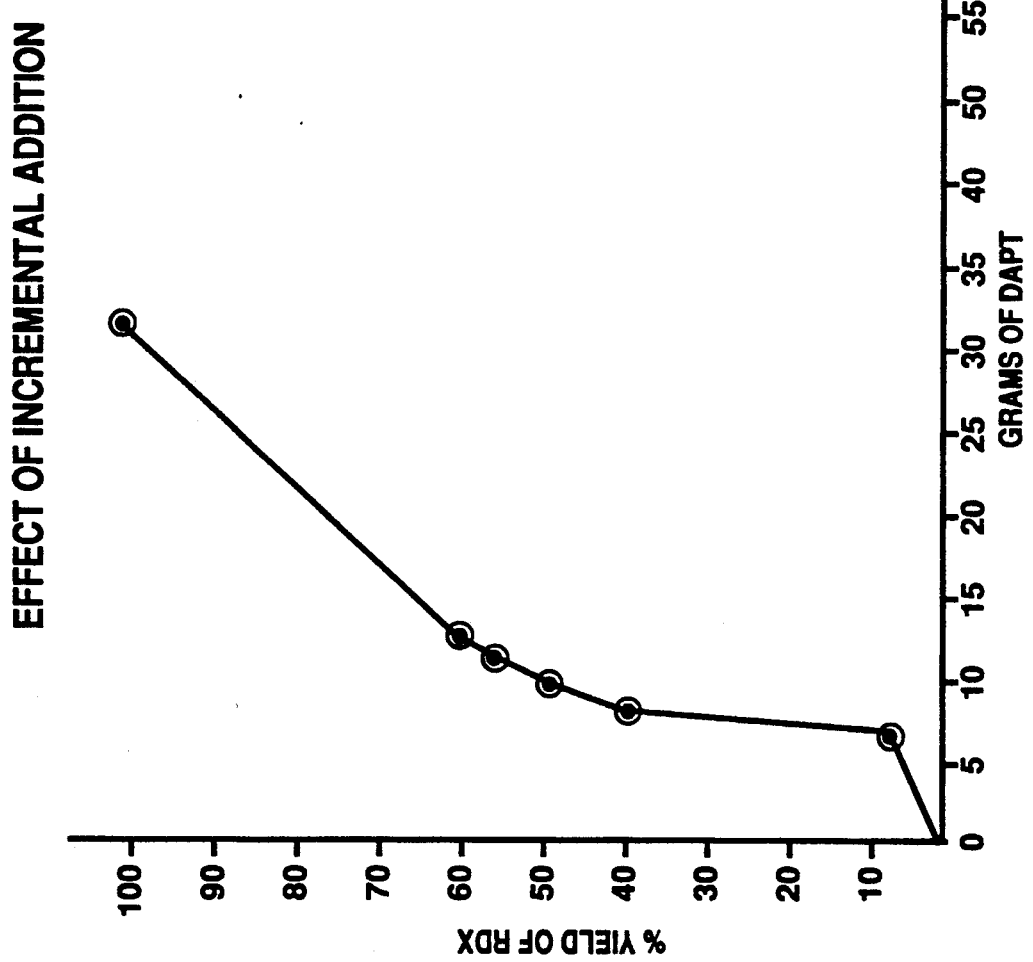

PROCESS FOR PREPARATION OF RDX

GOVERNMENTAL INTEREST

The invention described herein may be manufactured, used and licensed by or for the Government.

BACKGROUND OF THE INVENTION

Today, RDX is probably the most important high brisance explosive; its brisant power is high owing to its high density and high detonation velocity. It is relatively insensitive (as compared to say PETN, which is an explosive of a similar strength); it is very stable; its performance properties are only slightly inferior to those of the homologous Octogen (HMX).

In the prior art, RDX vis. hexamethylene tetramine is nitrated to hexogen by concentrated nitric acid. After the nitration mixture has reacted it is poured into cold water and the product is thereby caused to precipitate. In the conventional industrial practice hexamethylene tetraamine dinitrate is reacted with ammonium nitrate and the necessary excesses of nitric acid and acetic anhydride in acetic acid solvent medium, the hexogen is precipitated by addition of water, and the excess acetic anhydride is lost by hydrolysis to acetic acid. Waste acetic acid formed during the reaction is re-concentrated, and subjected to an energy intensive ketene process being thereby, converted back to useful acetic anhydride. The regenerated acetic anhydride is recycled back to the process. The yield of RDX is good, about 80% based upon two molecules of RDX per molecule of hexamine. The production of the prior process always contains some HMX contamination. The amount of HMX may vary greatly when enhanced by variation of the reaction conditions.

SUMMARY OF THE INVENTION

DAPT is an intermediate in the synthesis of HMX. Our method for the conversion of DAPT to RDX provides the "GARDEC PROCESS" a greatly expanded nitramine capability and does not require extensive duplication or modification of facilities when pure HMX is desired. In fact our yield of either RDX or HMX is quantitative. We have achieved at least 97% efficiency.

An object of the present invention is to provide a practical and cost effective process for preparing high yields of RDX from 3,7-DIACETYL 1,3,5,7-TETRAAZA[3.3.1]BICYCLONONANE (DAPT). Other objects will become apparent from the following description of the invention.

Outstanding features which are unique to this invention are the quantitative yield, reduced reactant requirements, and added flexibility; all due to the fact that we are starting with a preacetylated reactant.

The process of the present invention is considered to be unobvious in view of the fact that RDX formation does not follow logically as being readily derivable from the structure of DAPT. The structure of DAPT is such that those skilled in the field would generally conclude that it would naturally react instead to provide HMX. It is not apparent or easily explainable why the DAPT structure is so completely broken down and reassembled to provide very high yields of RDX.

DESCRIPTION OF THE PREFERRED EMBODIMENTS

The following examples illustrate specific embodiments of the method of carrying out the process of the present invention. It is to be understood that they are illustrative only and do not in any way limit the invention.

EXAMPLE 1—BACKGROUND

Note should be taken, our preparations of RDX have been accomplished on a 5-100 gram scale. On this scale no adverse reactions have been noticed which would indicate any safety hazard on scale-up. A 100 gram procedure based upon this work is as follows.

A 100 ml beaker is charged with 11.3 grams of DAPT dissolved in 6.8 grams of acetic acid. To this is added two reactant liquids. These liquids are added alternately and intermittently. Liquid one is comprised of 10.5 grams of ammonium nitrate and 13.1 grams of nitric acid. The second liquid is composed of 30 grams of acetic anhydride. The addition of these two liquids to the initial mixture produces an exotherm.

The temperature of the reaction is kept closely to 68 degrees Centigrade. Cooling is minimal and said cooling is only required from time to time. The addition sequence is started with the nitric acid/ammonium nitrate solution and is followed by the acetic anhydride. The nitric acid solution is added in small portions, as dictated by the exotherm, a gram or so at a time. After a couple of seconds the acetic anhydride is added stoichiometrically in a ratio of 1.8 moles acetic anhydride to 1.0 mole of ammonium nitrate and the cycle of addition of reactants continued. An initial unknown precipitate forms almost from the first addition of ammonium nitrate/nitric acid to the system. The precipitate redissolves and the solution clears. The solution remains clear until about 2/3 of the additional reactants are added. A second precipitate now forms which we discovered to be RDX. As the additions are continued the RDX precipitate will become noticeably heavier. After complete addition a small sample may be assayed. The moist filtered cake will be found to contain about 0.035 grams of RDX/gram of reaction mixture.

EXAMPLE 2

We found, using the method, reactants, and quantities as set forth in example 1, that by modifying and continuing the addition of the DAPT to the system, that the yield could be greatly improved. These results are set forth in Table 1.

TABLE 1

| SAMP. # | APPROXIMATE YIELD DATA | | | |
|---|---|---|---|---|
| | G CAKE/G MIX | RDX % YIELD | DAPT ADDITION | TOTAL G DAPT |
| 1 | 0.026 G | 7.6% | 11.3 G | 11.3 G |
| 2 | 0.136 G | 39% | 2.8 G | 14.1 G |
| 3 | 0.166 G | 48% | 2.8 G | 16.9 G |
| 4 | 0.196 G | 56% | 2.8 G | 19.7 G |
| 5 | 0.211 G | 60% | 2.8 G | 22.5 G |
| 6 | 0.339 G | 98% | 12.5 G | 35.0 G |

It is obvious from Table 1 that after the first addition of DAPT, very little RDX is formed. However, even small incremental increases of DAPT dramatically increases the RDX yield, as shown. As can be seen for a less that 10% increase in DAPT, we have achieved a 500% increase in yield. As dramatically shown in Table 1, the yield of RDX is dramatically increased by our method. Using the same method, reactants and quantities [except for incremental addition of DAPT]. It is readily observed that the concentration of RDX increases dramatically as soon as the first small portion of additional DAPT is made. By the time the last addition is made, the reacting mixture has about reached equilibrium. Further additions of reactants may now be continued indefinitely without a decrease in efficiency. Alternatively a portion of the reaction mixture may be taken out and identical processing being made to it. In other words, we may have a continuous process of a batch system if desired. This all depends upon requirements such as the quantity of product needed. The high level of efficiency will be maintained indefinitely so long as nothing is done to disrupt the equilibrium.

EXAMPLE 3

We found using, the method, and reactants as set forth in example 2, that the quantities of reactant liquids may be varied. The relative molar ratio of the two liquid reactant acetic anhydride and ammonium nitrate (dissolved in nitric acid) should not be varied and should be maintained within tight tolerance of 1.8 moles of acetic anhydride to 1.0 mole of ammonium nitrate. However, the tightly maintained ratio of these two reactants may be varied somewhat relative to the quantity of DAPT, such variation having little or no effect upon yield. The degree of variation may be within the range of about 4.2 to 5.8 moles of acetic anhydride per mole of DAPT and 1.88 to 2.59 moles of ammonium nitrate. with the latter corresponding and dependant upon the quantity of acetic anhydride used. On the other hand, the quantity of acetic acid and nitric acid used are of less critical importance and may be varied plus or minus about 25% without effecting the yield.

SUMMARY

In conclusion, the process of the present invention is an improvement on the prior art. Note should be taken that the use of hexamine instead of DAPT may result in violent eruptions from the solution. On the other hand, use of DAPT allows for invention to be simple, effective, efficient, and facile in use. It is very safe to carry out because of the much reduced exothermicity relative to the art. In fact, if a total nitramine facility were constructed, our RDX process would offer substantial savings. We get quantitative yields and in several cases the yields are greater than those achieved by other processes of the art.

What is claimed is:

1. The process of making RDX which comprises reacting DAPT with ammonium nitrate, nitric acid and acetic anhydride.
2. The process of claim 1 are listed below, in ratio;
   DAPT—about 1.0 mole
   Acetic Anhydride—about 4.2 to 5.8 moles
   Ammonium Nitrate—about 1.88 to 2.59 moles
   Nitric Acid—about 3.1 moles to 5.4 moles
3. The process of claim 1 wherein the ammonia is dissolved in the nitric acid.
4. The process of claim 2 wherein acetic acid is present between about 2 to 4 moles as a solvent.
5. The process of claim 1, wherein the reactants are present in the following amount;
   DAPT—1.0 moles
   Ammonium Nitrate—2.2 moles
   Nitric Acid—4.2 moles
   Acetic Anhyride—5.25 moles

* * * * *